(12) United States Patent
Aoki et al.

(10) Patent No.: US 8,808,625 B2
(45) Date of Patent: Aug. 19, 2014

(54) DISPENSING APPARATUS AND A DISPENSING METHOD

(75) Inventors: Hiroshi Aoki, Tsukuba (JP); Hiroaki Tao, Tsukuba (JP); Masaki Torimura, Tsukuba (JP); Takashi Ikeda, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 757 days.

(21) Appl. No.: 12/201,552

(22) Filed: Aug. 29, 2008

(65) Prior Publication Data

US 2009/0180930 A1 Jul. 16, 2009

(30) Foreign Application Priority Data

Jan. 11, 2008 (JP) ................................ 2008-004196

(51) Int. Cl.
| | |
|---|---|
| *G01N 21/00* | (2006.01) |
| *B01L 3/02* | (2006.01) |
| *G01N 1/00* | (2006.01) |
| *G01N 1/16* | (2006.01) |
| *G01N 1/26* | (2006.01) |
| *G01N 35/10* | (2006.01) |
| *B01L 3/00* | (2006.01) |
| *G01N 1/02* | (2006.01) |
| *G01F 25/00* | (2006.01) |
| *G01N 1/14* | (2006.01) |

(52) U.S. Cl.
USPC ............. 422/81; 422/521; 422/501; 422/509; 422/515; 422/520; 422/524; 436/180; 73/1.74; 73/64.56; 73/863.31; 73/864.24; 73/864.73

(58) Field of Classification Search
USPC ........... 422/81, 501, 509, 510, 511, 520, 521, 422/524, 525, 100; 73/1.74, 64.56, 863.31, 73/864, 864.02, 864.13–864.18, 864.24, 73/864.73; 436/54, 180
See application file for complete search history.

(56) References Cited

U.S. PATENT DOCUMENTS

| | | | | |
|---|---|---|---|---|
| 3,640,822 | A | * | 2/1972 | Hrdina .......................... 210/635 |
| 4,338,280 | A | * | 7/1982 | Ambers et al. ................ 422/68.1 |
| 5,312,757 | A | * | 5/1994 | Matsuyama et al. ............ 436/54 |

(Continued)

FOREIGN PATENT DOCUMENTS

| | | |
|---|---|---|
| EP | 0206945 | 12/1986 |
| JP | 55-004523 | 1/1980 |

(Continued)

OTHER PUBLICATIONS

Office Action in Japanese Patent Application No. 2008-258958 dated Nov. 16, 2012.

*Primary Examiner* — Jill Warden
*Assistant Examiner* — Brittany Fisher
(74) *Attorney, Agent, or Firm* — Venable LLP; Michael A. Sartori; Tamatane J. Aga

(57) ABSTRACT

In a dispensing apparatus for dispensing a liquid, such as a sample solution, on a substrate, such as a glass slide, the dispensing apparatus includes a capillary provided with a distal end and a proximal end, a pump unit configured to pump an operating liquid into the capillary and to pump the operating liquid out of the capillary, and a controller configured to control the pump unit so as to change a position of a liquid surface of the operating liquid in the capillary so that a predetermined volume of liquid is suctioned from the distal end into the capillary and the liquid suctioned in the capillary is discharged from the distal end. As a result, it is possible to precisely dispense extremely small volume amounts of liquids such as a nanoliter.

28 Claims, 19 Drawing Sheets

(56) References Cited

U.S. PATENT DOCUMENTS

| | | | |
|---|---|---|---|
| 5,656,493 A * | 8/1997 | Mullis et al. | 435/286.1 |
| 5,785,926 A * | 7/1998 | Seubert et al. | 422/518 |
| 6,083,763 A * | 7/2000 | Balch | 506/9 |
| 6,592,819 B1 | 7/2003 | Ogura | |
| 6,734,424 B2 * | 5/2004 | Lennon et al. | 250/288 |
| 6,983,636 B2 * | 1/2006 | Johnson et al. | 73/1.36 |
| 7,526,968 B2 * | 5/2009 | Lisec | 73/864.14 |
| 2001/0036424 A1 | 11/2001 | Takahashi et al. | |
| 2001/0036425 A1 | 11/2001 | Gazeau et al. | |
| 2002/0024347 A1 * | 2/2002 | Felici et al. | 324/754 |
| 2003/0155245 A1 * | 8/2003 | Morioka et al. | 204/601 |
| 2004/0072365 A1 * | 4/2004 | Rose et al. | 436/180 |
| 2006/0239863 A1 * | 10/2006 | Zach et al. | 422/100 |
| 2007/0122309 A1 * | 5/2007 | Nagai et al. | 422/63 |
| 2007/0212784 A1 | 9/2007 | Okun | |

FOREIGN PATENT DOCUMENTS

| | | |
|---|---|---|
| JP | 62-1459 | 1/1987 |
| JP | 9-318636 | 12/1997 |
| JP | 10-048100 | 2/1998 |
| JP | 10-096735 A | 4/1998 |
| JP | 10-293089 | 11/1998 |
| JP | 2001-074756 A | 3/2001 |
| JP | 2001-99847 | 4/2001 |
| JP | 2001-211873 | 8/2001 |
| JP | 2001-235400 A | 8/2001 |
| JP | 2003-315352 | 11/2003 |
| JP | 2005-91339 | 4/2005 |
| JP | 2007-139636 A | 6/2007 |
| JP | 2011-514439 A | 5/2011 |
| WO | WO 2008/007556 | 1/2008 |

* cited by examiner

RELATION BETWEEN
DISPENSING VOLUME AND VOLUME ERROR

| DISPENSING VOLUME | VOLUME ERROR (CV) |
|---|---|
| 100nL | 1.5nL (1.5%) |
| 50nL | 2.0nL (3.9%) |
| 20nL | 1.0nL (5.0%) |

FIG.18

DISPENSING APPARATUS AND A DISPENSING METHOD

This application claims the benefit of Japanese Patent Application No. 2008-004196, filed Jan. 11, 2008, which is hereby incorporated by reference herein in its entirety.

BACKGROUND OF THE INVENTION

1. Field of the Invention

The present invention is generally related to an apparatus and a method for suctioning a predetermined volume of liquid and discharging the suctioned liquid to a location to be dispensed.

2. Description of the Related Art

Currently, a high-throughput screening of biological samples and drug discovery samples, such as nucleic acids, proteins and peptides, and a comprehensive analysis of organisms are strongly needed. In addition, targets having unstable natures such as biologically relevant materials are often used as samples handled in those fields. In those fields, automatically dispensing apparatuses capable of dispensing multiple types of sample solutions in a narrow area such as several centimeters squares, on a substrate, such as a glass slide at a high density with a short cycle time are needed.

The automatically dispensing apparatus is typically provided with a dispensing head having a plurality of nozzles such as pipette chips, and automatically conduct a process of taking desirable volumes of sample solutions from a sample solution reservoir with the nozzles of the dispensing head, a process of dispensing the taken sample solutions from the nozzles at predetermined positions on a substrate, and a process of cleaning the nozzles or exchanging the nozzles into unused new nozzles. Standard microtiter plates having 96, 384 or 1,536 wells are typically used as a sample solution reservoir for containing the sample solutions. The wells in the microtiter plates are arrayed at array pitches of 9 mm, 4.5 mm or 2.5 mm.

Dispensing pitches when dispensing a liquid on the substrate are often from several tens of micrometers to several hundreds of micrometers. Therefore, when dispensing sample solutions contained in the sample solution reservoirs including the microtiter plates on a substrate, it is necessary to change the array pitch of the nozzles of the nozzle head.

For example, Japanese Patent Laid-Open No. 2001-99847 and Japanese Patent Laid-Open No. 2001-211873 disclose variable pitch mechanisms capable of change an array pitch between arrayed nozzles of a dispensing head.

However, in the variable pitch mechanisms, there is a limit on narrowing the array pitch, because the variable pitch mechanisms change the array pitch by moving the entire nozzles. Accordingly, it is difficult to adapt the variable pitch mechanisms to dispensing intervals of from several tens of to several hundreds of micrometers.

Additionally, in the above technical fields, it is required to control small dispensing amounts of liquids having at least a volume of microliter order, and it is also required to control extremely small dispensing amounts of liquid having a volume of nanoliter order.

However, it is difficult for the conventional automatically dispensing apparatuses to control precise dispensing amounts of liquids having a volume of nanoliter order.

SUMMARY OF THE INVENTION

An object of the present invention is to provide an apparatus and a method capable of precisely dispensing extremely small volume amounts of liquids having a small volume, such as a nanoliter.

Another object of the present invention is to provide an apparatus and method capable of dispensing liquids in a narrow area at a high density in a short cycle time.

The dispensing apparatus according to the present invention includes a capillary provided with a distal end and a proximal end; a pump unit configured to pump an operating liquid into the capillary and to pump the operating liquid out of the capillary; and a controller configured to control the pump unit so as to change a position of a liquid surface of the operating liquid filled in the capillary so that a predetermined volume of liquid is suctioned from the distal end into the capillary and that the liquid suctioned into the capillary is discharged from the distal end.

The dispensing method uses a capillary provided with a distal end and proximal end and a pump unit configured to pump an operating liquid into the capillary and to pump the operating liquid out of the capillary includes a step of filling the operating liquid from the pump unit to the capillary; a step of adjusting a position of a liquid surface of the operating liquid in the capillary to a position at a predetermined distance from the distal end;
a step of dipping the distal end of the capillary into a liquid; a step of changing the position of the liquid surface of the operating liquid by controlling the pump unit so that a predetermined volume of the liquid is suctioned from the distal end into the capillary; a step of moving the distal end of the capillary out of the liquid; and a step of changing the position of the liquid surface of the operating liquid by controlling the pump unit so that the liquid suctioned into the capillary is discharged from the distal end on a predetermined location.

According to the present invention, because a position of a surface of an incompressible operating liquid in a capillary is controlled so that a liquid is suctioned from a distal end of the capillary and that the suctioned liquid in the capillary is discharged from the distal end of the capillary, a extremely small and precise volume of the liquid can be dispensed.

Further, according to the present invention, because a dispensing pitch is adjustable due to flexibility of the capillaries, the liquid can be dispensed from the distal ends of the capillaries in a narrow area at a high density.

Still further features of the present invention will become apparent from the following description of exemplary embodiments with reference to the attached drawings.

Further features of the present invention will become apparent from the following description of exemplary embodiments (with reference to the attached drawings).

BRIEF DESCRIPTION OF THE DRAWINGS

FIG. 11B is a cross-sectional view of the distal end portion of the capillary when the suction of the sample solution into the capillary is completed;

FIG. 18 is a table indicating relationships between dispensing volumes and dispensing errors based on the result of FIG. 15 to FIG. 17.

DESCRIPTION OF THE EMBODIMENTS

An embodiment of the present invention will be described below in detail with reference to the attached drawings.

Figure 1:
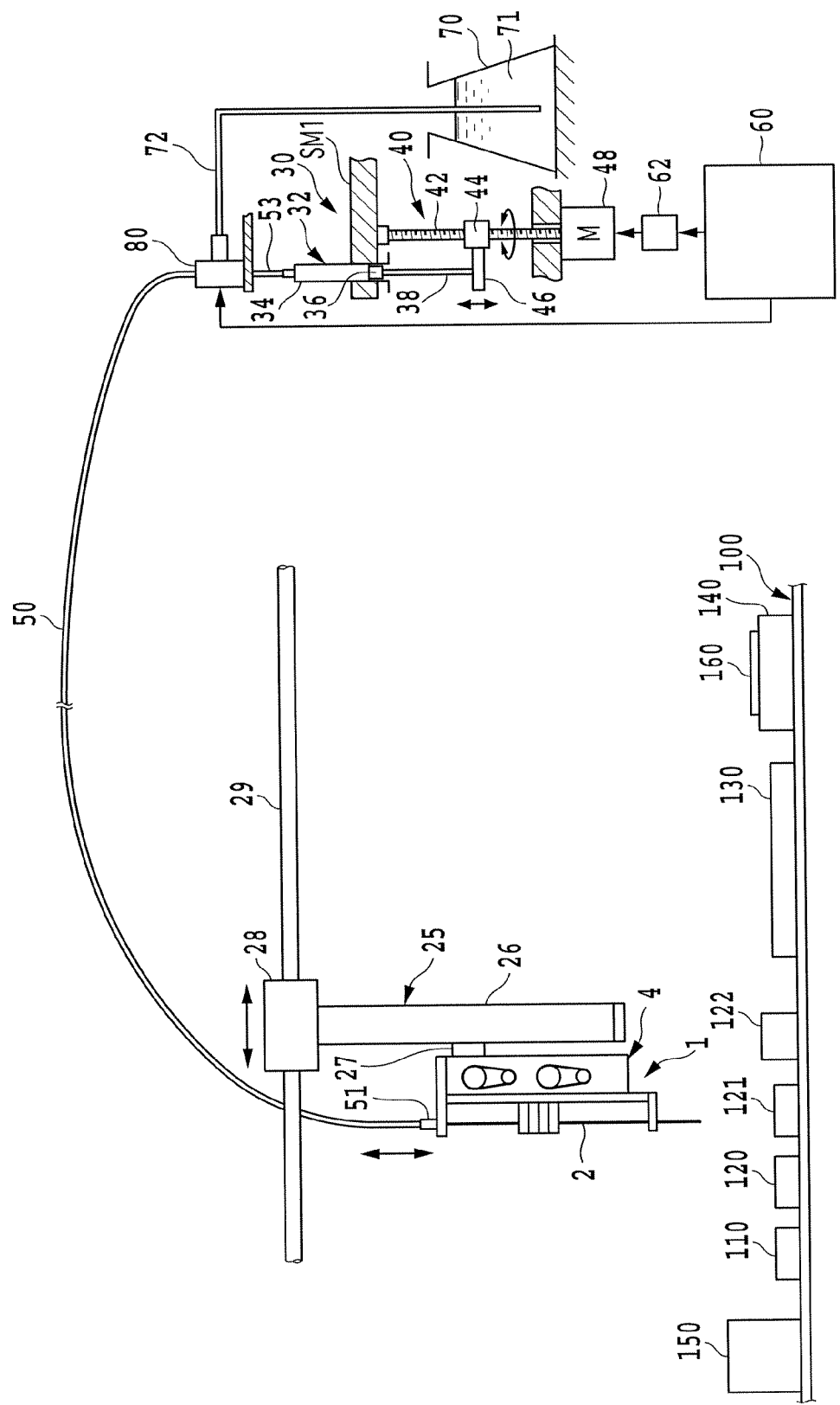
FIG. 1 is a schematic view of a dispensing apparatus according an embodiment of the present invention.

FIG. 1 is a schematic view of a dispensing apparatus according to an embodiment of the present invention.

The dispensing apparatus includes a dispensing head 1 holding a plurality of capillaries 2, a movement mechanism 25 for moving and positioning the dispensing head 1, a pump unit 30, a controller 60, an operating liquid tank 70 and a table 100 arranged below the dispensing head 1. A waste liquid reservoir 110, a cleaning liquid reservoir 120, an alcohol reservoir 121, a blower 122, a microtiter plate 130, a holder 140 and a cutting device 150 are arranged on the table 100.

Figures 2A, 2B:
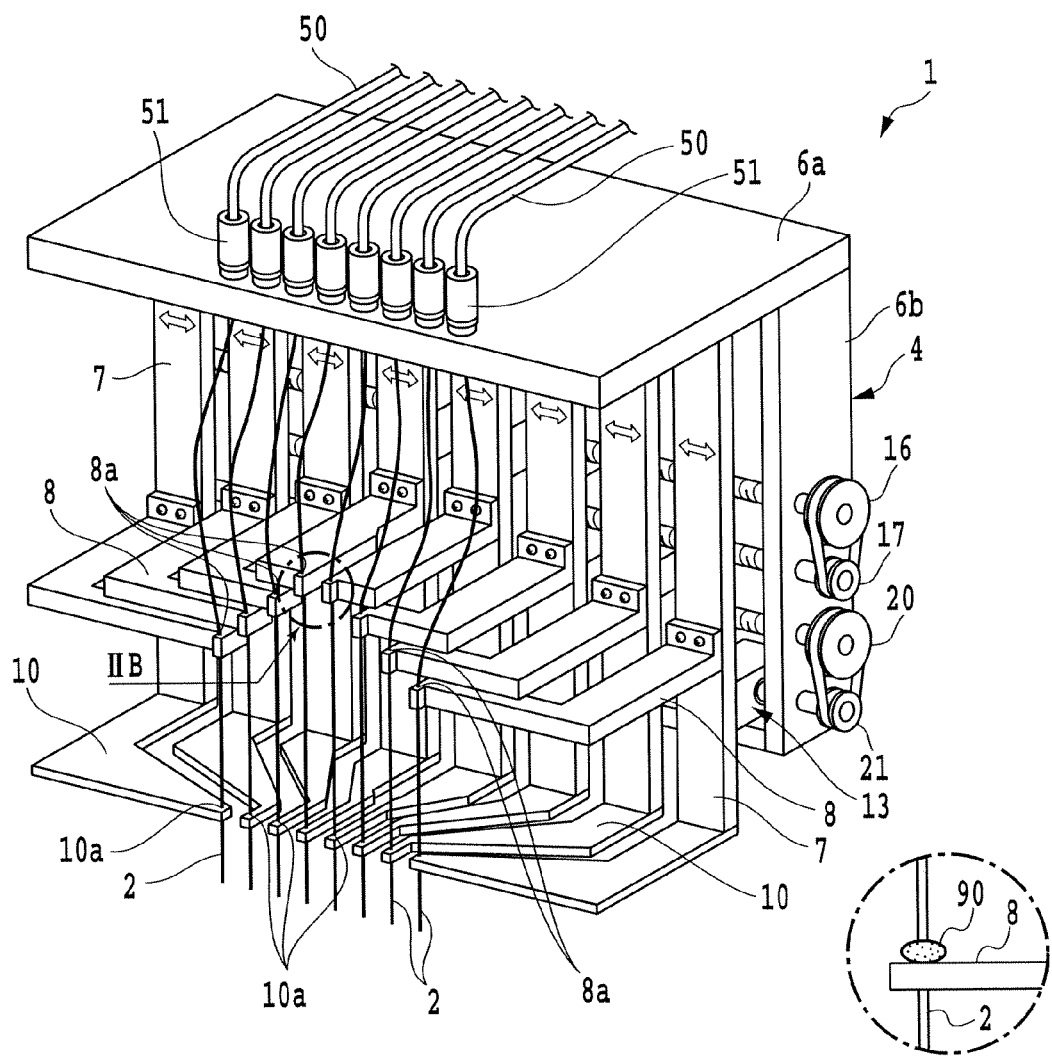
FIG. 2A is a perspective view of a dispensing head in the dispensing apparatus shown in FIG. 1.
FIG. 2B is an enlarged view a front end portion of an upper guiding member of FIG. 2A.

FIG. 2 is a perspective view of the dispensing head 1.

The dispensing head 1 includes the plurality of capillaries 2 regularly arrayed in a line, a plurality of lower guiding members 10 for defining an array pitch of the distal ends of the capillaries 2, a plurality of upper guiding members 8 disposed above the lower guiding members 10 for guiding the capillaries 2 so as to keep the capillaries 2 in a straight line in cooperation with the lower guiding members 10, a plurality of movable frames 7 arranged at a regular interval for supporting the lower and upper guiding members 10 and 8, and a variable pitch mechanism 4 for moving the movable frames 7 so as to change the array pitch of the distal ends of the capillaries 2.

Figure 3:
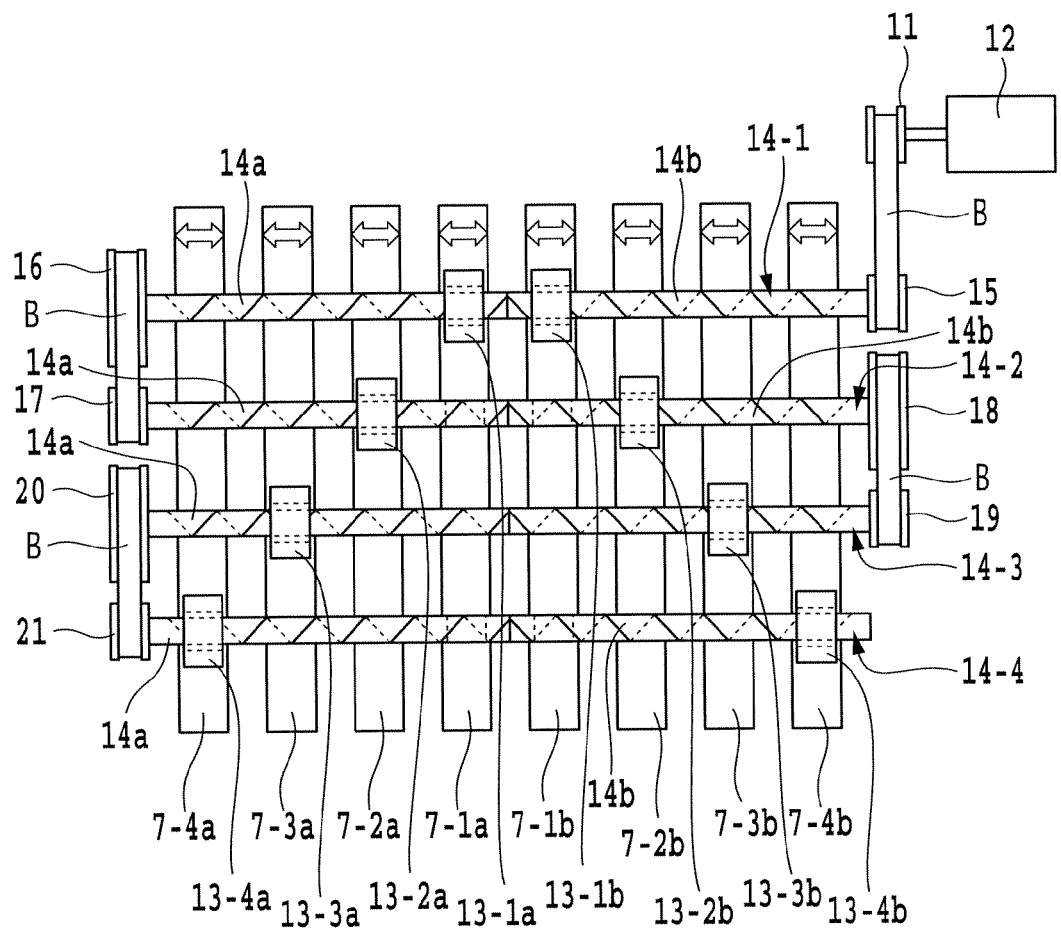
FIG. 3 is a back view of a variable pitch mechanism, with which the dispensing head shown in FIG. 2 is provided.

FIG. 3 is a back view of the variable pitch mechanism 4.

As shown in FIG. 2 and FIG. 3, the variable pitch mechanism 4 is provided with a plurality of screw shafts 14 arranged in parallel and rotatably supported at both ends thereof by lower frames 6b, a plurality of movable members 13 respectively connected with the plurality of movable frames 7 and respectively engaged with the screw shafts 14, pulleys 15 to 21 respectively attached at the ends of the screw shafts 14, a motor 12 for inputting a rotational torque to one of the screw shafts 14, a pulley 11 attached at an output shaft of the motor 12, and pulley belts B wounded around the above pulleys 11, 15 to 21.

Each of the screw shafts 14 has a screw portion 14a threaded on one side from a center position in the longitudinal direction and a screw portion 14b threaded on the other side from the center position. The screw portion 14a and 14b have the same pitch but are threaded in opposite directions to each other. The movable members 13-1a to 13-4a and the movable members 13-1b to 13-4b, which are engaged with the screw portions 14a and the screw portions 14b of the screw shafts 14-1 to 14-4, are symmetrically-arranged about the center position in the longitudinal direction of the screw shafts 14, respectively. Additionally, the movable members 13-1a to 13-4a are connected to the frame 7-1a to 7-4a, respectively, and the movable members 13-1b to 13-4b are connected to the frame 7-1b to 7-4b, respectively.

Diameter ratios between the pulley 16 and the pulley 17, between the pulley 18 and the pulley 19 and between the pulley 20 and the pulley 21 are respectively set at 3:1, 5:3 and 7:5. Accordingly, a ratio between rotational speeds of the screw shafts 14-1 to 14-4 is 1:3:5:7.

Because the screw portions 14a and 14b are threaded in opposite directions with respect to each other, the movable members 13-1a to 13-4a engaged with the screw portions 14a are moved in directions opposite to that of the movable members 13-1b to 13-4b engaged with the screw portions 14b, respectively. Each two movable members 13-1a and 13-1b to 13-4a and 13-4b engaged with the common screw shafts 14-1 to 14-4 are moved close to or away from each other in accordance with a direction of rotation of the motor 12. Additionally, a ratio between the movement amounts of the movable members 13-1 to 13-4 engaged with the screw shafts 14-1 to 14-4, respectively, is 1:3:5:7.

In the variable pitch mechanism 4, when the movable frames 7-1a and 7-1b are moved by a distance of x and a pitch between the movable frames 7-1a and 7-1b is changed by a distance of 2x, the two movable frames 7-2a and 7-2b, 7-3a and 7-3b, and 7-4a and 7-4b are moved by distances of 3x, 5x, and 7x, respectively. As a result, a pitch between the movable frames 7 adjacent to each other can be changeable and intervals between the movable frames 7 adjacent to each other can be kept equal.

Each of the lower guiding member 10A is fixed to a lower end portion of each of the movable frames 7 at a proximal end portion thereof so as to extend in a horizontal direction, and is provided with guide hole 10a, into which the capillary 2 is inserted, at a front end portion thereof. Additionally, the lower guiding members 10 are disposed on a common plane and formed in shapes so as not to be mutually interfered with to each other when a pitch between the guide holes 10a adjacent to each other is minimized.

Each of the upper guiding members 8 is fixed to half way portion of each of the movable frames 7 at a proximal end portion thereof so as to extend in a horizontal direction, and is provided with guide hole 8a into which the capillary 2 is inserted. The guide holes 8a are located at positions corresponding to the guide holes 10a, respectively. Additionally, the upper guiding members 8 are fixed at different heights of the movable frames 7 so as to avoid mutual interferences therebetween when a pitch between the guide holes 8a adjacent to each other is minimized, respectively.

Each of the capillaries 2 is provided with a liquid flow passage, is flexible, and is formed of a material such as stainless steel, fused silica glass, synthesized silica glass or the like. For dispensing an extremely small volume of a liquid, the inner diameter of the capillary 2 is preferably set at a diameter within a range of from nanometers to micrometers. However, the inner diameter of the capillary 2 is not limited to this range. The dimensions of the capillary 2 such as an inner diameter, an outer diameter and length are optimized, for example, in accordance with a volume of liquid to be dispensed by the capillary 2.

As shown in FIG. 2, each of the plurality of capillaries 2 is connected to each of a plurality of joints 51 arranged on an upper frame 6a at a proximal end thereof so as to downwardly extend from the upper frame 6a, pass through the guide holes 8a of the upper guiding members 8 and the guide hole 10a of the lower guiding members 10, and is free at a distal end thereof. Each of the capillaries 2 is guided by the hole 8a and the guide hole 10a, so that a lower portion of the capillary 2 below the guide hole 1a is kept in a straight line. A stopper 90 is attached to each of the capillaries 20 so as to regulate a displacement of each of the capillaries 20 in a height direction with respect to the guiding member 8, so that a height of the distal end of the capillary 2 is defined. Note that the position of the stopper 90 to be attached is not limited to this configuration and can be modified as needed.

Figure 4A:
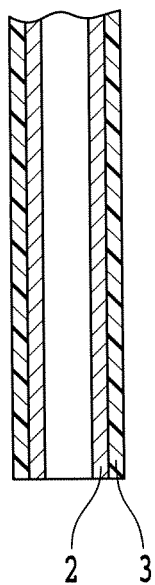
FIG. 4A is a cross-sectional view of an example of a structure of a distal end portion of a capillary.

FIG. 4A is a cross-sectional view illustrating a configuration of a distal end of the capillary 2.

The capillary is covered with a reinforced layer 3 on an outer surface thereof. The reinforced layer 3 is formed of a resin such as polyimide resin and a fluorocarbon polymer. The reinforced layer 3 coated on the outer surface of the capillary 2 can prevent the capillary 2 from being subjected to a plastic deformation and can provide the capillary 2 with an increased restoring ability.

Figure 4B:
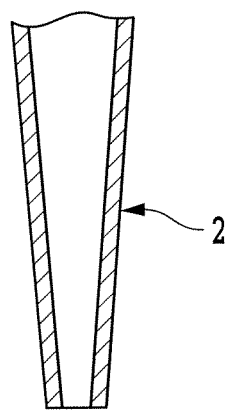
FIG. 4B is a cross-sectional view of another example of a structure of a distal end portion of a capillary.

FIG. 4B is a cross-sectional view of another configuration of the distal end portion of the capillary 2.

As shown in FIG. 4B, it is also possible to form the capillary 2 so that inner diameters of the capillary 2 gradually decreases toward the distal end. As a result, the size of a droplet of liquid formed at the distal end of the capillary 2 can be reduced.

Additionally, a hydrophobic treatment also can be applied to the capillary 2 at least on the distal end portion thereof so as to promote separation of a liquid therefrom. The hydrophobic treatment is a chemical modification, a depositing of silicon analogue, a coating of fluorocarbon polymer or the like, onto the outer surface and/or the inner surface of the capillary 2.

As shown in FIG. 1 and FIG. 2, each of the capillaries 2 is connected to each of the connecting tubes 50 via each of the joint 51. Each of the connecting tubes 50 is connected with the pump unit 30 via the three-way valves 80.

Each of the connecting tube 50 is flexible and is formed of a resin such as a polyether ether ketone (PEEK). PEEK can provide the connecting tube 50 with the flexibility required to move the dispensing head 1 and to suppress a deformation of the connecting tube 50 caused by the pressure of an operating liquid as little as possible, such pressure being applied on the connecting tube 50 when dispensing a liquid. As a result, a precise volume of a liquid to be dispensed can be controlled.

As shown in FIG. 1, the movement mechanism 25 includes a frame 26 movably holding a movable member 27 connected with the dispensing head 1, a rail 29 arranged in a horizontal direction, and a slider 28 holding the frame 26 and movably arranged along the rail 29.

The frame 26 incorporates a mechanism configured with a motor for moving the movable member 27 in a vertical direction, and the like.

The slider 28 incorporates a mechanism configured with a motor for moving the slider 28 along the rail 29, and the like.

The pump unit 30 is provided with a plurality of syringe pumps 32 and an actuator for driving the syringe pumps 32.

Each of the syringe pumps 32 has a syringe barrel 34, a plunger tip 36 fitted with an inner surface of the syringe barrel 34, and a plunger rod 38 connected to the plunger tip 36.

Each of the syringe barrels 34 is connected to the three-way valve via a connecting tube 53.

Figure 5:
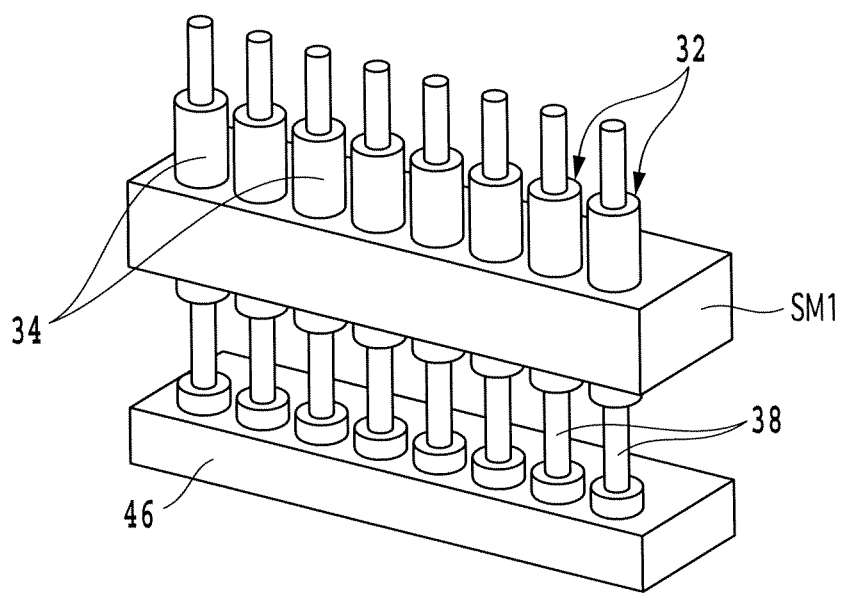
FIG. 5 is a perspective view of a syringe pump.

As shown in FIG. 5, the plurality of syringe barrels 34 is commonly supported by supporting members SM1 and the plurality of plunger rods 38 is commonly connected to a movable plate 46.

The actuator 40 includes a rotatably supported screw shaft 42, a movable member 44 engaged with the screw shaft 42 and connected to the above movable member 44, and a stepping motor 48 for rotating the screw shaft 42.

The stepping motor is driven by being supplied with a driving current in accordance with a control command from the controller 60. When the stepping motor 48 is driven, the movable plate 46 is moved so as to push and pull the plunger rods 38 back and forth.

Each of the three-way valves 80 is connected with each of the connecting tubes 50, each of the syringe barrels 34, and each of conduit tubes 72 communicated with the operating liquid tank 70. The three-way valve 80 is an electromagnetic or electric type, and alternatively connects between the syringe barrel 34 and the connecting tube 50 or between the syringe barrel 34 and the conduit tube 72.

The operation liquid is an incompressible liquid, preferably water.

The waste liquid reservoir 110 receives a waste liquid to be discharged from the capillaries 2.

The cleaning liquid reservoir 120 stores a cleaning liquid, such as water, for cleaning the distal end portions of the capillaries 2.

The alcohol reservoir 121 reserves an alcohol used for cleaning the distal end portions of the capillaries 2.

The blower blows dry and inert gas, such as nitrogen gas, so as to blow off a liquid adhered to the distal end portions capillaries 2.

The microtiter plate 130 is provided with a plurality of wells, in which sample solutions are contained.

The holder 140 holds a glass slide 160 on which the sample solutions are dispensed.

The cutting apparatus 150 cuts the distal end portions of the capillaries 2 with a laser beam, cutting blades or the like. For example, a cutting of the distal ends of the capillaries 2 after dispensing can eliminate the need for cleaning the distal ends of the capillaries 2 and can provide an alignment between the distal ends of the capillaries 2.

The controller 60 is configured with hardware such as a processor and a memory, necessary software and the like. The controller 60 provides a driver 62 with pulse commands so as to control the stepping motor 48. The controller 60 also provides the three-way valves 80 with control commands so as to operate the three-way valves 80. The controller 60 also provides the movement mechanism 25 with control commands so as to control a position of the dispensing head 1.

Next, the operation of the above dispensing apparatus will be explained with reference to FIG. 6 to FIG. 14. Note that the controller 60 controls a sequence of operations of the dispensing apparatus.

Figure 6:
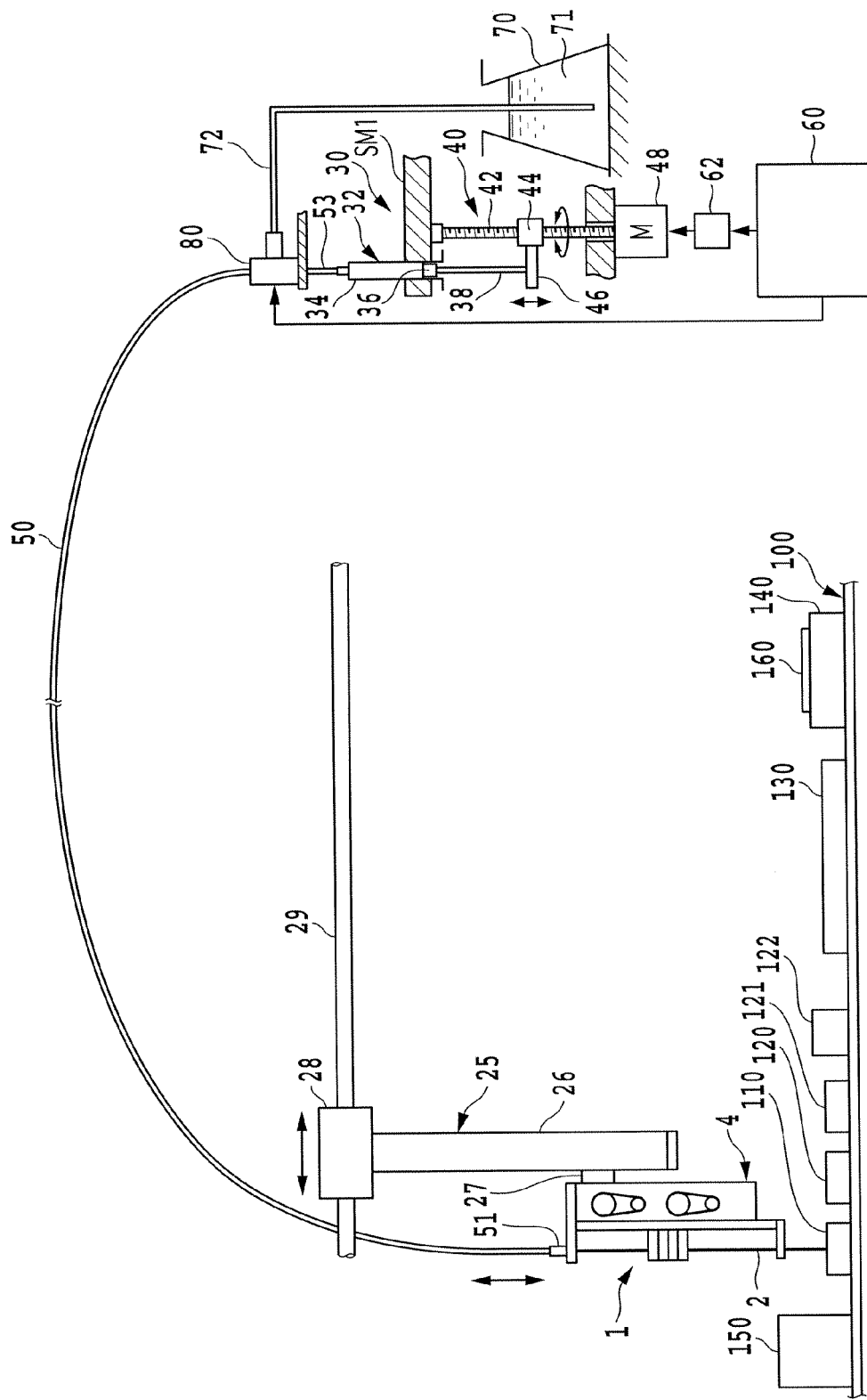
FIG. 6 is a view showing that the capillary of the dispensing apparatus shown in FIG. 1 is positioned to a waste liquid reservoir.

To fill the capillaries 2, the connecting tubes 50 and the syringe pumps 32 with an operating liquid 71, as shown in FIG. 6, the dispensing head 1 is moved by the movement mechanism 25 so that the distal ends of the capillaries 2 are positioned in the waste liquid reservoir 110.

To fill the capillaries 2, the connecting tubes 50 and the syringe pumps 32 with an operating liquid 71, first, the three-way valves 80 is controlled so as to communicate each of the syringe pumps 32 with each of the conduit tubes 72.

Next, the stepping motor 48 is driven so as to pull the plunger tips 36 backward, so that the operating liquid 71 is pumped from the operating liquid tank 70 into the syringe barrels 36.

Next, each of the three-way valves 80 is controlled so as to communicate each of the syringe pumps 32 with each of the connecting tubes 50, while the stepping motor 48 is driven so as to push the plunger tip 36 forward, so that the operating liquid 71 in each of the syringe barrels 36 is pumped into both of each of the connecting tubes 50 and each of the capillaries 2.

Figure 7A:
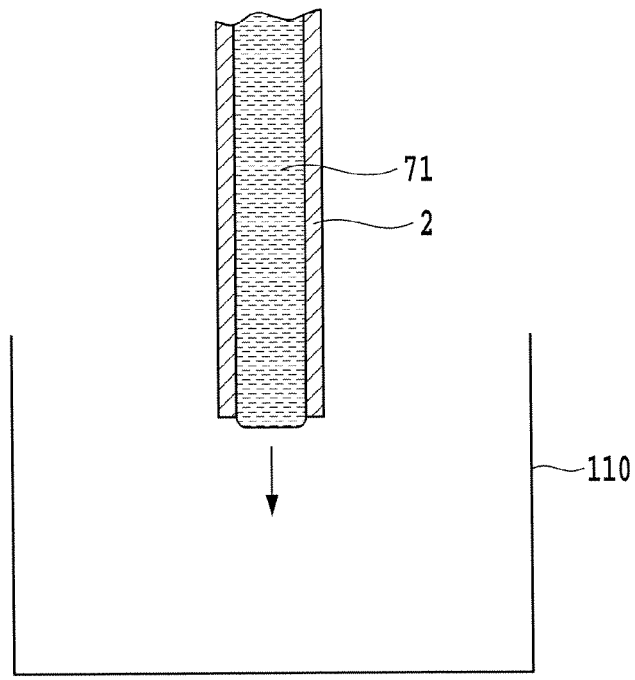
FIG. 7A is a cross-sectional view of the distal end portion of the capillary when filling an operating liquid therein.

In the foregoing procedure, it is repeated as many times as needed to pump the operating liquid 71 into each of the syringe barrels 36 and to pump the operating liquid 71 out of each of the syringe barrels 36 into each of the connecting tubes 50, so that the operating liquid 71 is discharged from each of the distal ends of the capillaries 2 into the waste liquid reservoir 110, as shown in FIG. 7A. When the operating liquid 71 is discharged from each of the distal ends, an air existing in each of the capillaries 2, each of the connecting tubes 50 and each of the syringe pumps 32 is also discharged together with the operating liquid 71 to the exterior. As a result, all of the interior spaces of each of the capillaries 2 and each of the connecting tubes 50 is filled with the operating liquid 71.

Figure 7B:
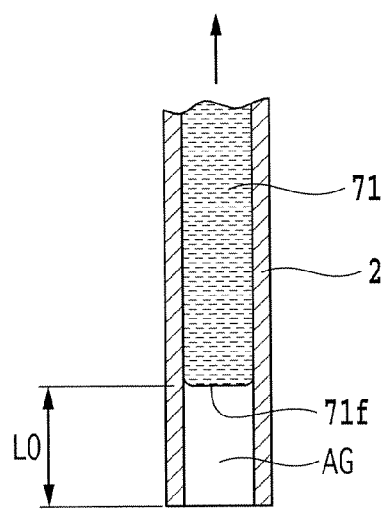
FIG. 7B is a cross-sectional view of the distal end portion of the capillary when adjusting a position of the liquid surface of the operating liquid to a position a predetermined distance from the distal end.

Next, the stepping motor 48 is driven so as to pull the plunger tips 36 backward and to raise the position of liquid surface 71$f$ of the operating liquid 71 in each of the capillaries 2, so that an air gap AG is formed in each of the capillaries 2, as shown in FIG. 7B. The position of the liquid surface 71$f$ of the operating liquid 71 is controlled so as to make a length from the distal end of the capillaries 2 to the liquid surface 71$f$ equal to a predetermined length L0. The predetermined length L0 is preferably set within a range of from several millimeters to several centimeters; however it is not limited to this range.

Figure 8:
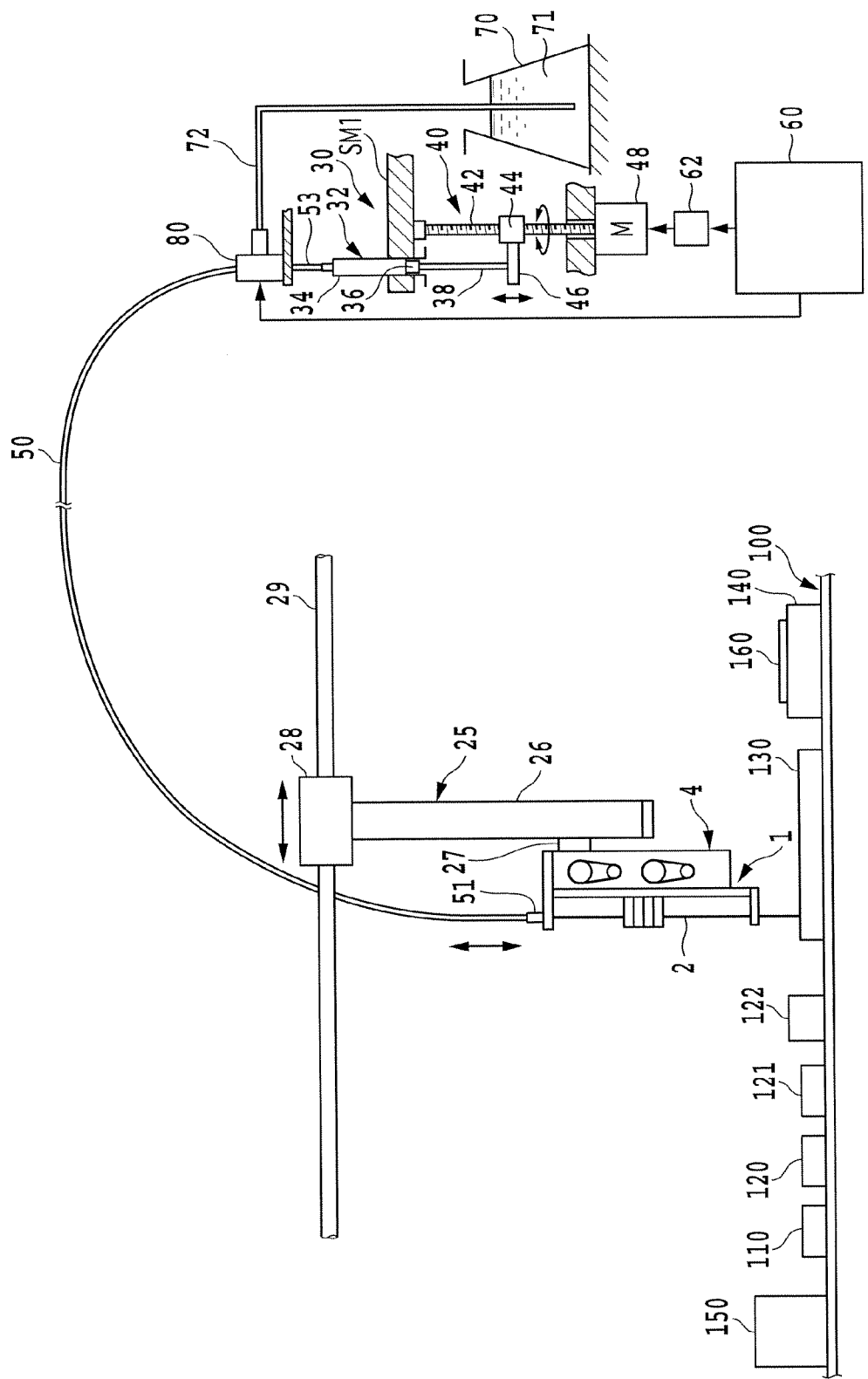
FIG. 8 is a view showing a state that a sample solutions is pumped into the capillary of the dispensing apparatus shown in FIG. 1 positioned at a microtiter plate.
Figure 9:
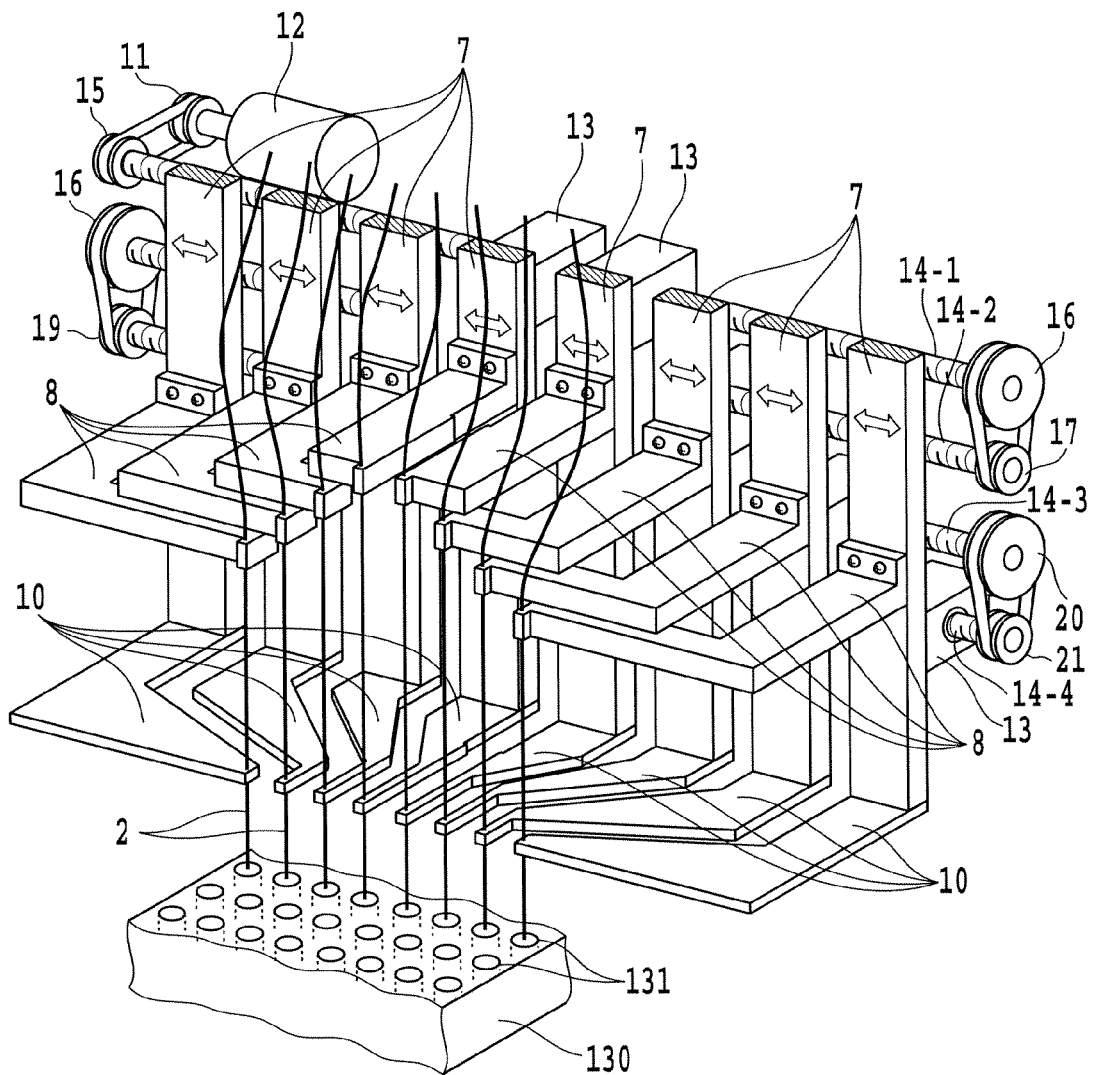
FIG. 9 is a view showing a state of the dispensing head shown in FIG. 8.
Figure 10A:
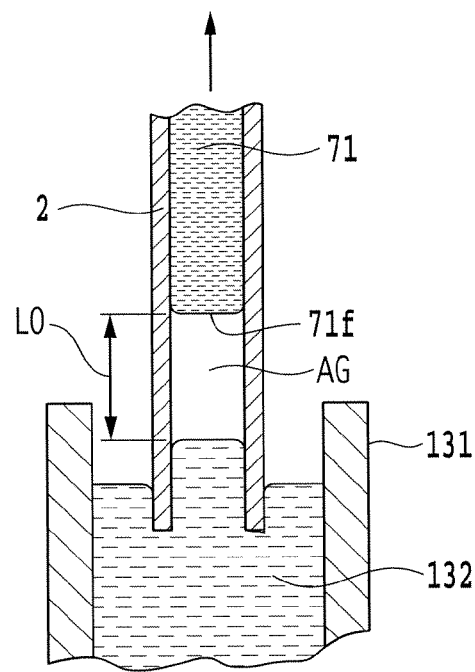
FIG. 10A is a cross-sectional view of the distal end portion of the capillary when the sample solution is suctioned into the capillary.

After the liquid surface 71$f$ of the operating liquid 71 in the capillary 2 is adjusted, an array pitch of capillaries 2 of the dispensing head 1 is adjusted so as to correspond to an array pith of wells 131 arrayed on the microtiter plate 130. Next, as shown in FIG. 8 and FIG. 9, the dispensing head 1 is moved toward the microtiter plate 130 so as to locate each of the distal ends of the capillaries 2 into each of the corresponding wells 131 of the microtiter plate 130. As a result, as shown in FIG. 10A, each of the distal ends of the capillaries 2 is dipped into a sample solution 132 contained in each of the wells 131.

Next, the stepping motor 48 is driven so as to pull the plunger tip 36 backward and to raise the position of the liquid surface 71$f$ of the operating liquid 71 in each of the capillaries 2, so that a predetermined volume of the sample solution 132 is suctioned into each of the capillaries 2. When the sample solution 132 is suctioned into each of the capillaries 2, as shown in FIG. 10A, the air gap AG exists between the suctioned sample solution 132 into each of the capillaries 2 and the liquid surface 71$f$ of the operating liquid 71 therein.

Accordingly, the operating liquid 71 is not mixed into the sample solution 132 suctioned into the capillary 2.

Figure 10B:
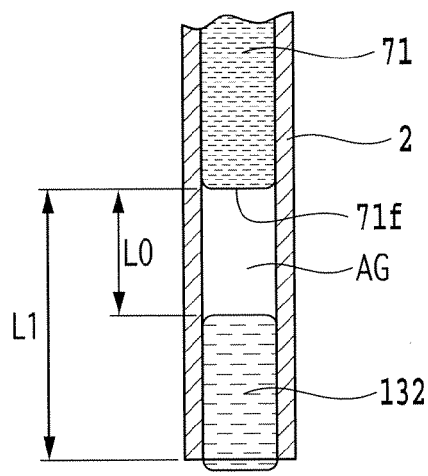

As shown in FIG. 10B, the position of the liquid surface 71$f$ of the operating liquid 71 is controlled so as to make a length from the distal end of the capillaries 2 to the liquid surface 71$f$ equal to a predetermined length L1, so that a predetermined volume of the sample solution 132 is suctioned into the capillary 2. As a result, the sample solution 132 is precisely measured in volume.

Figure 11:
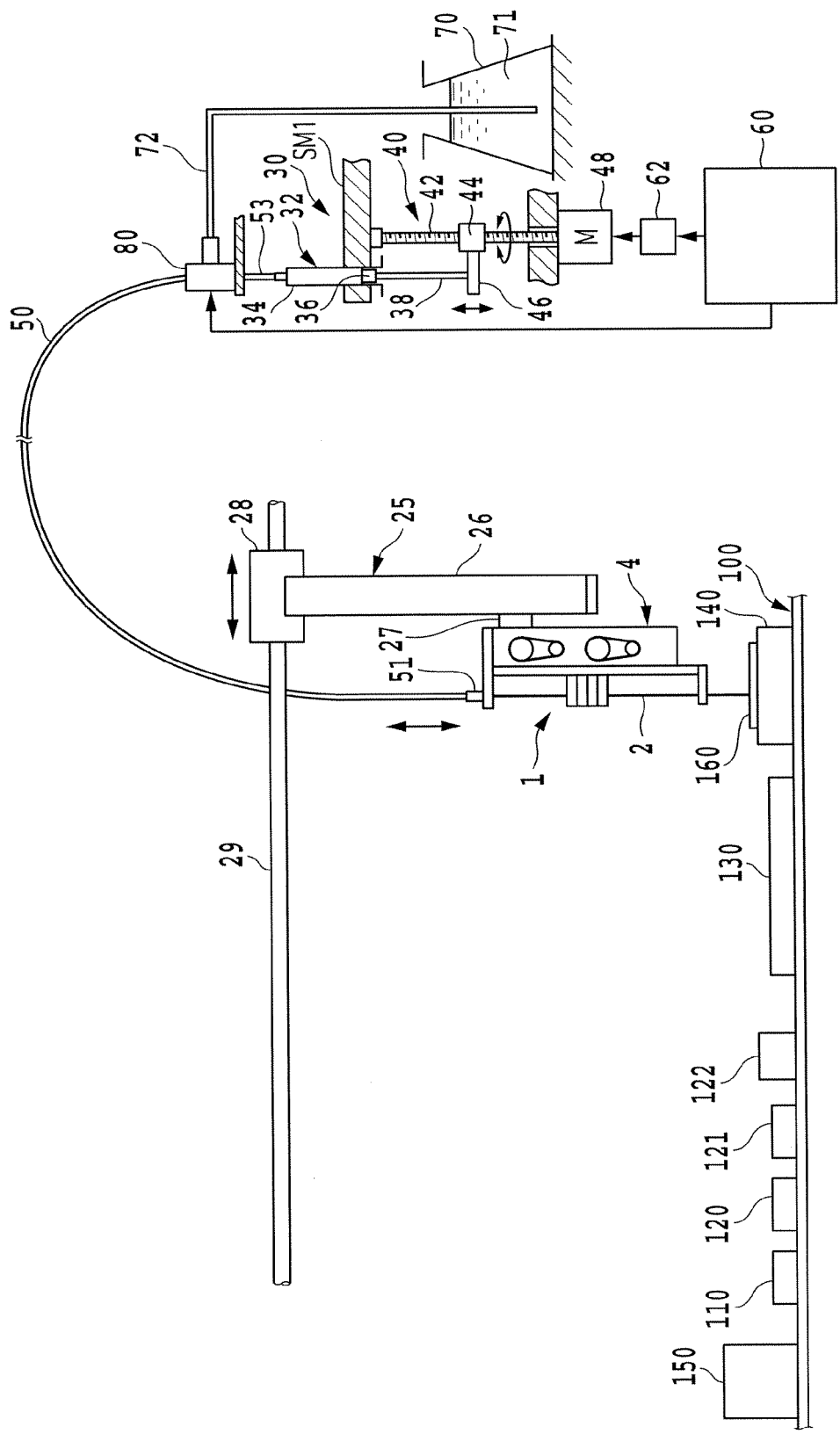
FIG. 11 is a view showing that the dispensing apparatus is dispensing on a glass slide from the distal end of the capillary positioned above the glass slide.
Figure 12:
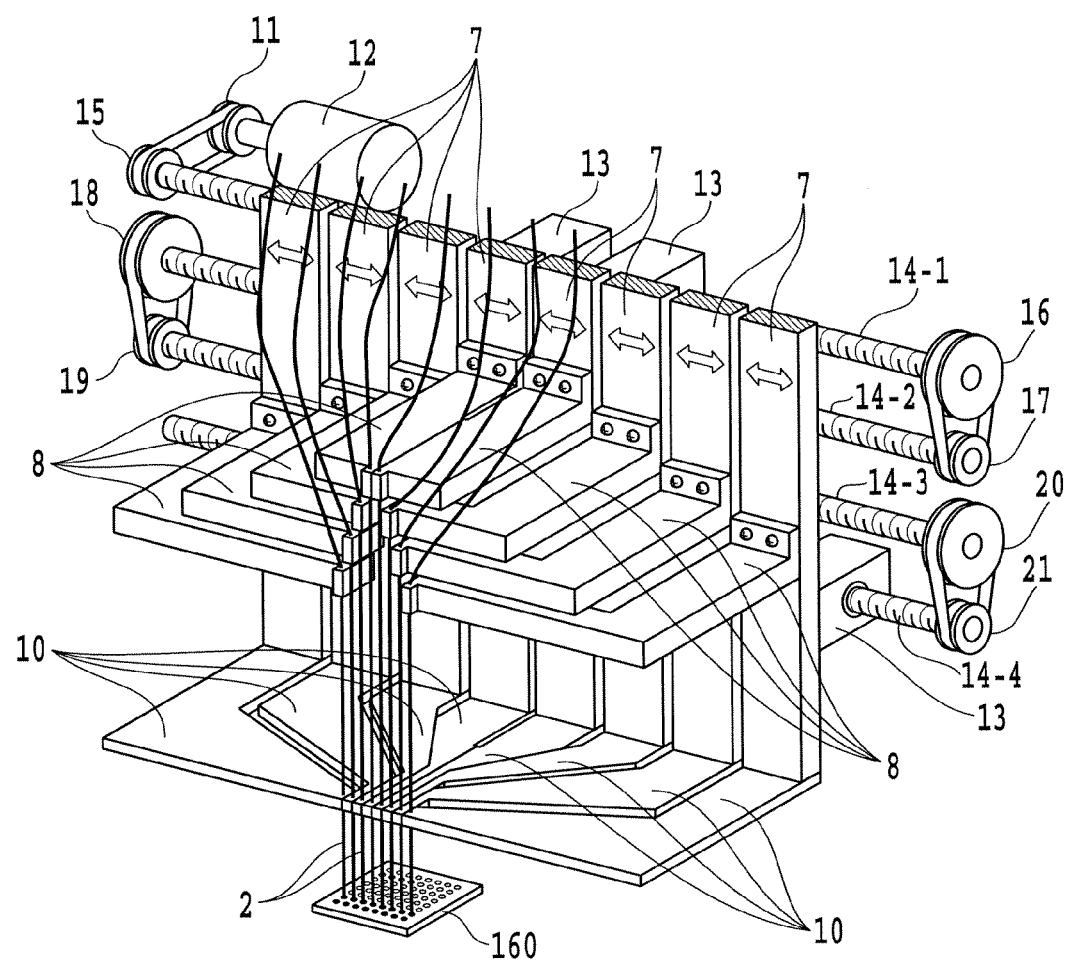
FIG. 12 is a perspective view of a state of the dispensing head in the dispensing apparatus shown in FIG. 11.

Next, as shown in FIG. 11, the dispensing head 1 is moved by the movement mechanism 25 so as to draw up the distal end of each of the capillaries 2 from each of the wells 131 and to position the distal end above the glass slide 160. The array pitch of the distal ends of the capillaries 2 is narrowed in accordance with a dispensing pitch onto the glass slide 160, as shown in FIG. 12. When the array pitch at the distal end sides of the capillaries 2 is narrowed, a portion guided by the guiding member 8 and 10 of each of the capillaries 2 is kept in a straight line; however an upper portion above the guiding member 8 is deflected. The deflection of each of the capillaries 2 allows to narrow the array pitch of the distal ends of the capillaries 2.

Figure 13:
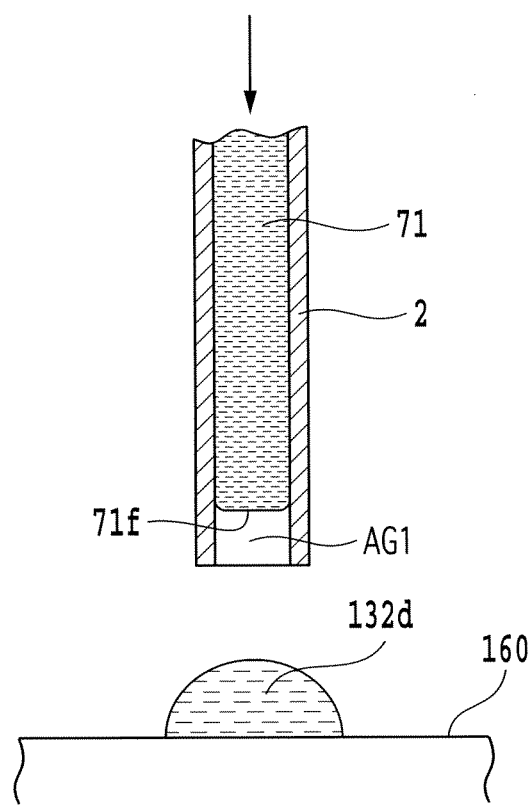
FIG. 13 is a cross-sectional view of the distal end portion of the capillary when discharging the sample solution suctioned into the capillary.

Next, the stepping motor 48 is driven so as to push the plunger tip 36 forward and lower the position of the liquid surface 71$f$ of the operating liquid 71 in each of the capillaries 2, so that the entire volume of the sample solution 132 suctioned into each of the capillaries 2 is discharged onto the glass slide 160. As shown in FIG. 13, droplets 132$d$ of the sample solutions 132 from the plurality of capillaries 2 are simultaneously dispensed on the glass slide 160. The position of the liquid surface 71$f$ of the operating liquid 71 after discharging the sample solution 132 is controlled so as to form an air gap AG1 in each of the capillaries 2, so that it is prevented the operation liquid 71 from falling off onto the glass slide 160.

The distal end of each of the capillaries 2 is cleaned after discharging the sample solution 132 onto the glass slide 160.

To clean the distal end portion of each of the capillaries 2, as shown in FIG. 6, the dispensing head 1 is moved by the movement mechanism 25 so as to position the distal ends of the capillaries 2 into the waste liquid reservoir 110. Then a part of the operating liquid 71 in each of the capillaries 2 is discharged from the distal end so as to clean the interior thereof.

Figure 14:
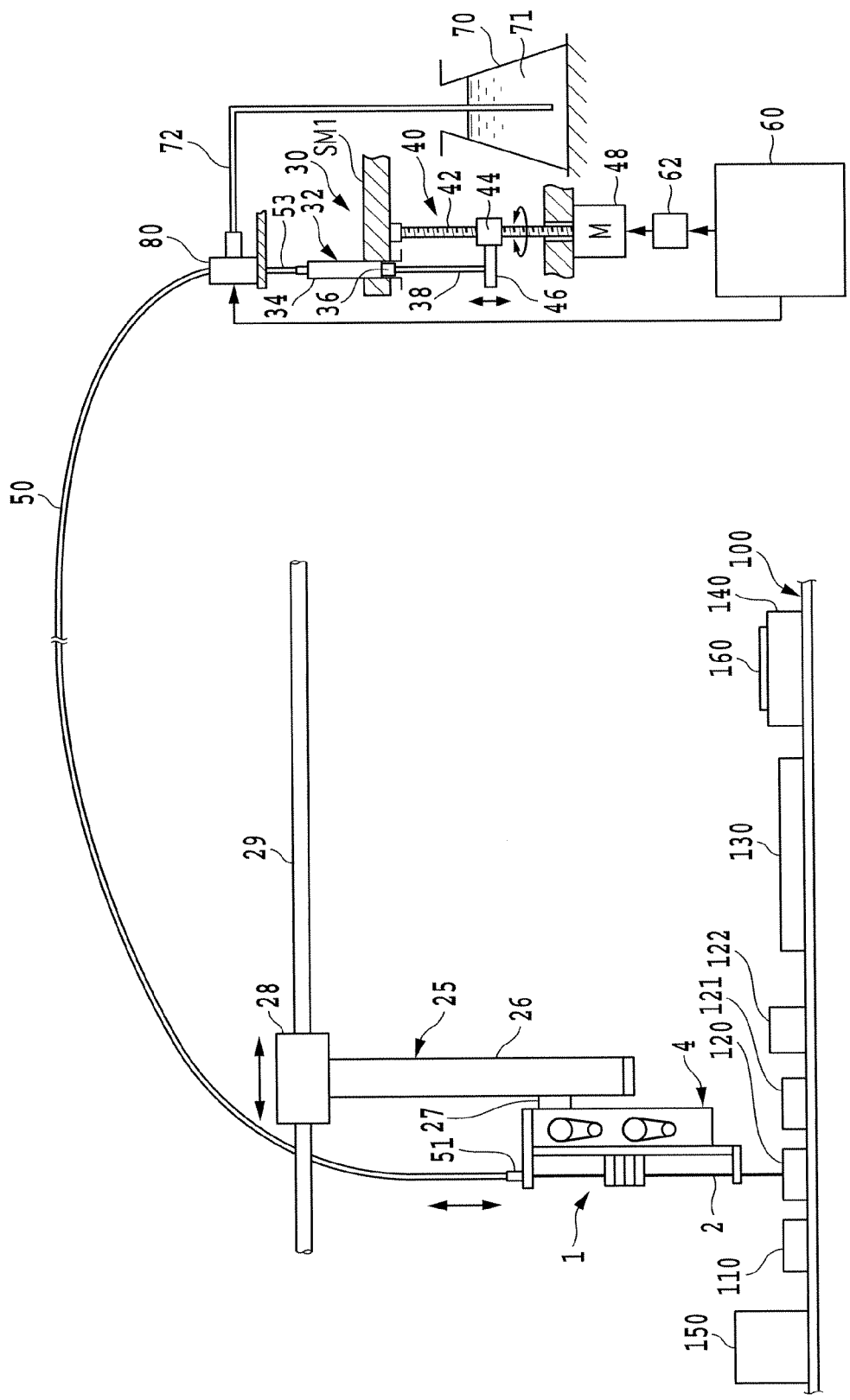
FIG. 14 is a view showing that the capillary of the dispensing apparatus of FIG. 1 is positioned to a cleaning liquid reservoir.

Next, as shown in FIG. 14, the dispensing head 1 is moved by the movement mechanism 25 so as to position the distal ends of the capillaries 2 into the cleaning liquid reservoir 120, and then the outer peripheries of the distal end portions of the capillaries 2 are cleaned with a cleaning liquid. Next, the distal ends of the capillaries 2 are moved into the alcohol reservoir 121 so as to clean the distal ends of the capillaries 2 with alcohol. Finally, the distal ends of the capillaries 2 are moved into the blower 122 so that any liquid adhered on the distal ends of the capillaries 2 will be blow off.

The dispensing apparatus repeatedly performs the above operations, so that any necessary numbers of droplets of the sample solutions 132 are arrayed on the glass slide 160 in a matrix.

In the above embodiment, a required volume of the sample solution 132 for a single dispensation at a time is suctioned into the capillary 2 and the entire volume of the suctioned sample solution 132 in the capillary 2 is discharged onto the glass slide 160. However, the present invention is not limited to the configuration. For example, the controller 60 can control the pump unit 30 so that a required volume of the sample solution 132 for multiple dispensations is suctioned from the distal end into the capillary 2 at one time and the suctioned sample solution 132 in the capillary 2 is sequentially discharged from the distal end by a predetermined volume onto predetermined locations in the glass slide 160 in the multiple dispensations. In this configuration, it is possible to more rapidly dispense a required number of droplets of the sample solution 132 on the glass slide 160.

Next, result of the measurement regarding the dispensing accuracy of the dispensing apparatus according to the present embodiment will be explained with reference to FIG. 15 to FIG. 18.

Capillaries 2 having an outer diameter of 360 µm, an inner diameter of 150 µm and a length of about 20 cm were used for the measurement.

Figure 15:
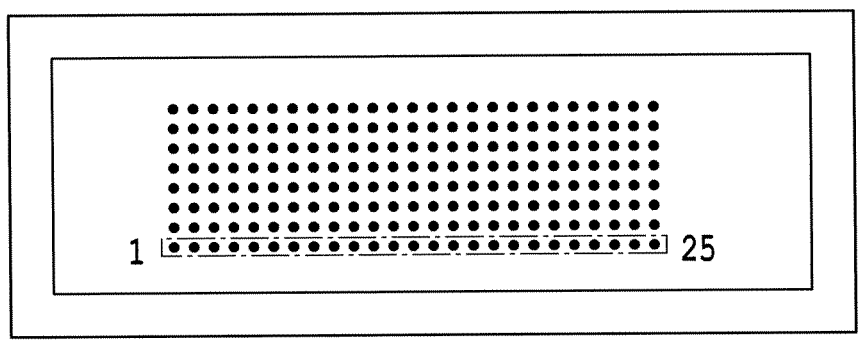
FIG. 15 is a plan view of a glass slide on which the sample solutions are dispensed under a specific condition by the dispensing apparatus of FIG. 1.
Figure 16:
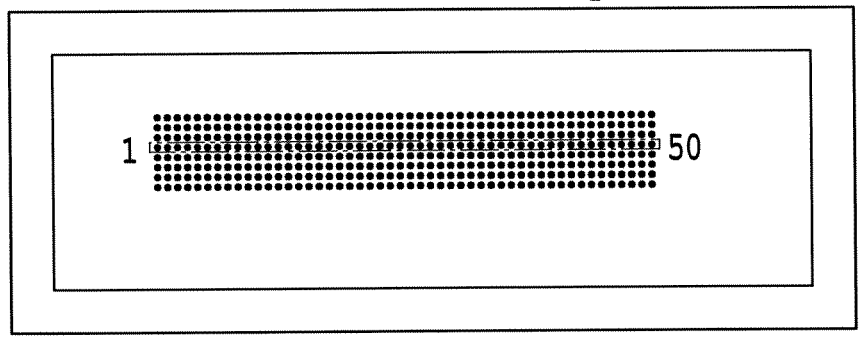
FIG. 16 is a plan view of a glass slide on which the sample solutions are dispensed under another specific condition by the dispensing apparatus of FIG. 1.
Figure 17:
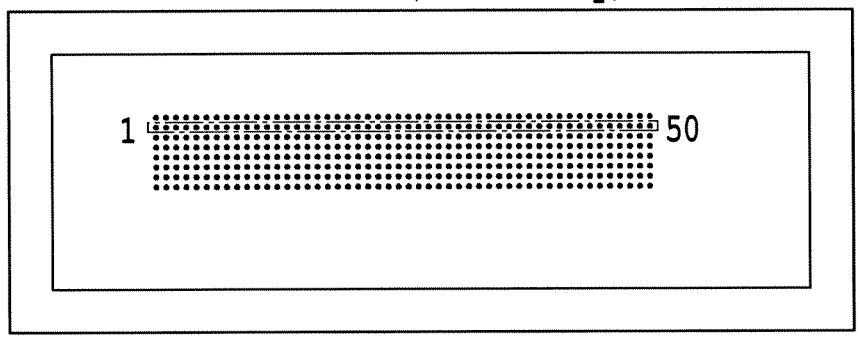
FIG. 17 is a plan view of a glass slide on which the sample solutions are dispensed under still another specific condition by the dispensing apparatus of FIG. 1.

FIG. 15 shows a glass slide on which spots arrayed in an 8 by 25 matrix at a pitch of 2.0 mm with a volume of 100 nanoliters of the sample solution. FIG. 16 shows a glass slide on which spots arrayed in an 8 by 50 matrix at a pitch of 1.0 mm with a volume of 50 nanoliters of the sample solution. FIG. 17 shows a glass slide on which spots arrayed in an 8 by 50 matrix at a pitch of 1.0 mm with a volume of 20 nanoliters of the sample solution.

The volume of each of the 25 or 50 spots of the sample solution, which are dispensed from the common capillaries on the slide glasses shown in FIG. 15 to FIG. 17, was measured.

FIG. 18 indicates the measured result. In FIG. 18, it is found that the dispensing errors are lower than 2.0 nanoliters, i.e. 5% in a coefficient of variation (CV).

The dispensing errors in the conventional and commonly marketed dispensing apparatuses are from about 50 to 250 nanoliters for dispensing from 1 to 10 microliters according to catalogues of the product makers thereof. Accordingly, the dispensing apparatus according to the present invention can remarkably improve the dispensing accuracy.

Figure 19:
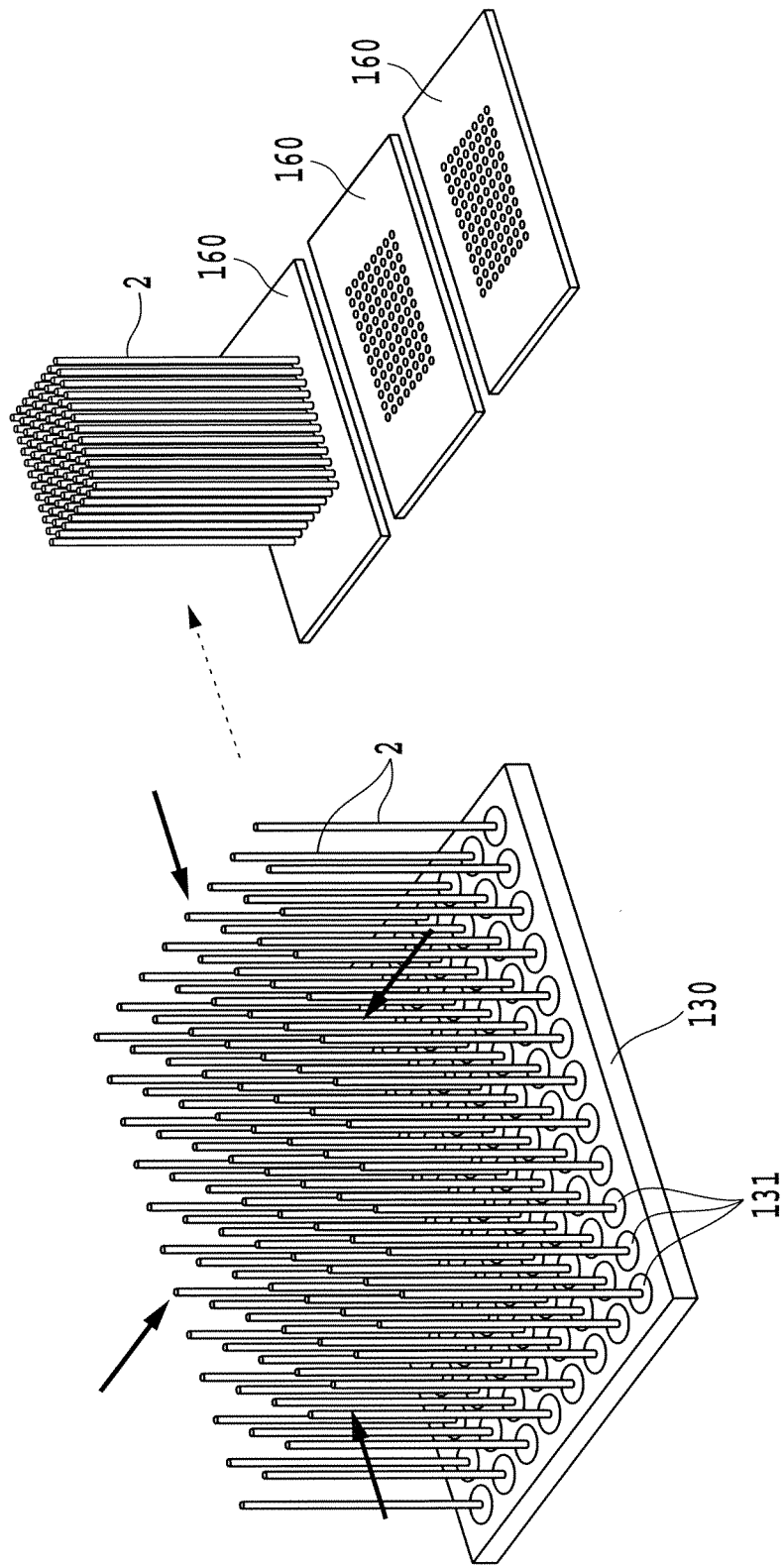
FIG. 19 is a perspective view showing a concept of a dispensing head according to another embodiment of the present invention.

In the above embodiment, the plurality of capillaries 2 are arranged in a line, however, the present invention is not limited to this configuration. For example, as shown in FIG. 19, the same number of capillaries 2 as the numbers of wells 131 arranged in a matrix in the microtiter plate 130 are provided to a dispensing head (not shown). Additionally, the dispensing head is provided with a variable pitch mechanism (not shown) capable of changing the pitch of the plurality of capillaries 2 arranged in a matrix. As the variable pitch mechanism, for example, mechanisms disclosed in International Publication Number WO 2008/007556 and Japanese Patent Laid-Open No. 2001-99847 can be used. In this configuration, when the array pitch is decreased, it is possible to simultaneously dispense a large number of droplets in a narrow area on the glass slide 160 so as to be arrayed in a matrix.

In the above embodiment, the syringe pump is used as a pump; however, the present invention is not limited to this configuration. A tubing pump, a screw pump, a gear pump or the like also can be used. In addition, the syringe pumps 32 were commonly driven; however, the syringe pumps 32 also can be individually driven.

In the above embodiment, the actuator transforms a rotational movement of the motor into a linear movement; however, a linear actuator such as a linear motor also can be used. In addition, the three-way valve or other elements of the present invention also can be manually operated.

In the above embodiment, the movement mechanism can move the dispensing head in the vertical and horizontal directions; however, a three dimensional movement mechanism can be used.

In the above embodiment, an explanation was made in the case where the dispensing head is moved, however, the present invention is not limited to this configuration. For example, a configuration can be employed that the dispensing head is fixed and that the table holding the microtiter plate, the glass slide or the like is moved.

In the above embodiment, the array pitch of the distal ends of the capillaries was decreased; however, the array pitch of the distal ends of the capillaries also can be increased.

In the above embodiment, the dispensing apparatus was provided with a plurality of capillaries; however, the present invention is not limited to this configuration. For example, the apparatus can be provided with a single capillary. In this configuration, a movement mechanism for changing a position of the distal end of the single capillary can be employed.

In the above embodiment, the first and second guiding members were used as guiding members of the present invention; however, the present invention is not limited to this configuration. For example, a common guiding member can be used for defining a position of the distal end of the capillary and keep the distal end portion of the capillary in a straight line.

In the above embodiment, the proximal ends of the capillaries were arranged by a predetermined pitch; however, the present invention is not limited to this configuration. For example, a configuration that the proximal ends of the capillaries are fixed to random positions, and the distal ends of the capillaries are arranged with a predetermined pitch can be employed.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined by appended claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A dispensing apparatus, comprising:
   a capillary provided with a distal end and a proximal end;
   a pump unit configured to pump an operating liquid into the capillary and to pump the operating liquid out of the capillary;
   a controller configured to control the pump unit so as to change a first position of a liquid surface of the operating liquid in the capillary so that a predetermined volume of a liquid is suctioned from the distal end into the capillary and to change a second position of the liquid surface of the operating liquid in the capillary so that the liquid suctioned into the capillary is discharged from the distal end, wherein the capillary is flexible, the proximal end of the capillary is communicated with the pump unit and fixed at a predetermined position, and a position of the distal end of the capillary in a horizontal plane is variable due to a deflection of the capillary; and
   a changing mechanism configured to change the position of the distal end of the capillary from one position to another position without changing a position of the proximal end of the capillary for suction or discharging of a liquid from the distal end outlet using a deflection of the capillary,
   wherein the changing mechanism comprises a horizontally movable member which engages with the capillary between the distal and proximal ends of the capillary, and
   the deflection of the capillary is caused by the member.

2. The dispensing apparatus according to claim 1, wherein the controller controls the position of the liquid surface of the operating liquid in the capillary so as to provide an air gap between the liquid suctioned into the capillary and the operating liquid in the capillary.

3. The dispensing apparatus according to claim 1, wherein the controller controls the pump unit so that a required volume of the liquid for multiple dispensations is suctioned from the distal end into the capillary in a single suction and that the suctioned liquid in the capillary is discharged from the distal end by a predetermined volume in multiple dispensations.

4. The dispensing apparatus according to claim 2, wherein the controller controls the pump unit so that a part of the operating liquid in the capillary is discharged from the distal end after an entire volume of the liquid suctioned into the capillary is discharged.

5. The dispensing apparatus according to claim 1, wherein the operating liquid is an incompressible liquid.

6. The dispensing apparatus according to claim 1, further comprising a filling unit configured to transfer the operating liquid from the pump unit to the capillary.

7. The dispensing apparatus according to claim 6, wherein the filling unit includes a three-way valve connected to a supply source of the operating liquid, the capillary and the pump unit.

8. The dispensing apparatus according to claim 1, further comprising a guiding member configured to guide the capillary so as to define the position of the distal end thereof.

9. The dispensing apparatus according to claim 1, further comprising a guiding member configured to guide the capillary so as to keep at least distal portion of the capillary in a straight vertical line.

10. The dispensing apparatus according to claim 1, further comprising a stopper configured to regulate a displacement of at least distal portion of the capillary in a height direction so as to define a height of the distal end of the capillary.

11. The dispensing apparatus according to claim 1, further comprising a position changing mechanism adapted to change a position of the changing mechanism and, thus, the distal end of the capillary, in a vertical direction.

12. The dispensing apparatus according to claim 1, further comprising a plurality of capillaries, wherein an array pitch of the distal ends of the capillaries is adjustable due to a deflection of each of the plurality of capillaries.

13. The dispensing apparatus according to claim 1, further comprising a plurality of capillaries regularly arrayed, wherein an array pitch of the distal ends of the capillaries can be elongated and contracted with respect to an array pitch of the proximal ends.

14. The dispensing apparatus according to claim 13, further comprising a plurality of guiding members configured to define the array pitch of the distal ends of the capillaries.

15. The dispensing apparatus according to claim 13, further comprising a plurality of first guiding members, the first guiding member configured to guide the capillaries so as to define the array pitch of the distal ends of the capillaries; and
a plurality of second guiding members, the second guiding member configured to guide the capillaries so as to keep the capillaries in a straight line in cooperation with the first guiding member.

16. The dispensing apparatus according to claim 14, further comprising a variable pitch mechanism configured to move the plurality of the first and second guiding members so as to change the array pitch of the distal ends of the capillaries.

17. The dispensing apparatus according to claim 16, wherein the variable pitch mechanism comprises a plurality of movable members, each of the movable members being connected to each of the plurality of first and second guiding members;
a plurality of screw shafts arranged parallel to each other, the screw shaft being rotatably supported and provided with a first and second screw portions threaded in directions opposite to each other, the first and second screw portions being respectively engaged with the movable members;
a plurality of rotation transmission mechanisms transmitting rotational torque between the screw shafts adjacent to each other; and
a motor configured to input rotational torque to one of the plurality of screw shafts.

18. The dispensing apparatus according to claim 1, further comprising a flexible connecting tube configured to connect the capillary with the pump unit, wherein the connecting tube is made of polyether ether ketone (PEEK).

19. The dispensing apparatus according to claim 1, wherein the pump unit comprises a plurality of pumps; and
a common actuator is used for driving the plurality of pumps.

20. The dispensing apparatus according to claim 19, wherein the plurality of pumps comprise syringe pumps.

21. The dispensing apparatus according to claim 1, wherein
the capillary is covered with a resin at least in a distal end portion thereof so as to increase a restoring ability thereof.

22. The dispensing apparatus according to claim 1, wherein a hydrophobic treatment is applied to the capillary at least on the distal end portion so as to promote a separation of the liquid therefrom.

23. The dispensing apparatus according to claim 1, wherein an inner diameter of the capillary gradually decreases toward the distal end.

24. The dispensing apparatus according to claim 1, further comprising a cutting unit configured to cut the distal portion of the capillary.

25. A dispensing method using a capillary provided with a distal end and a proximal end and a pump unit configured to pump an operating liquid into the capillary and to pump the operating liquid out of the capillary, the capillary being flexible, the proximal end of the capillary being fixed at a predetermined position, and a position of the distal end of the capillary in a horizontal plane being variable due to a deflection of the capillary, comprising steps of:
transferring the operating liquid from the pump unit to the capillary;
adjusting a position of a liquid surface of the operating liquid in the capillary to a position at a predetermined distance from the distal end;
dipping the distal end of the capillary into a liquid;
changing the position of the liquid surface of the operating liquid by controlling the pump unit so that a predetermined volume of the liquid is suctioned from the distal end into the capillary;
moving the distal end of the capillary out of the liquid;
changing the position of the liquid surface of the operating liquid by controlling the pump unit so that the liquid suctioned into the capillary is discharged from the distal end on a predetermined location;
varying a position of the distal end of the capillary by deflecting the capillary; and
changing the position of the distal end of the capillary via a changing mechanism from one position to another position without changing a position of the proximal end of the capillary for suction or discharging of a liquid from the distal end outlet using a deflection of the capillary, wherein the changing mechanism comprises a horizontally movable member which engages with the capillary between the distal and proximal ends of the capillary, and the deflection of the capillary is caused by the member.

26. The dispensing method according to claim 25, further comprising a step of discharging a part of the operating liquid in the capillary from the distal end so as to clean an interior of the capillary after an entire volume of the liquid suctioned into the capillary is discharged.

27. The dispensing method according to claim 25, further comprising a step of cutting off the distal end portion of the capillary exposed to the liquid.

28. The dispensing method according to claim 25, further comprising a step of adjusting an array pitch of the distal ends of a plurality of regularly arrayed capillaries by deflecting the capillaries.

* * * * *